United States Patent
Wan

(10) Patent No.: US 9,348,976 B2
(45) Date of Patent: May 24, 2016

(54) INFORMATION PROCESSING METHOD AND ELECTRONIC DEVICE

(71) Applicants: Beijing Lenovo Software Ltd., Beijing (CN); Lenovo (Beijing) Co., Ltd., Beijing (CN)

(72) Inventor: Xi Wan, Beijing (CN)

(73) Assignees: Beijing Lenovo Software Ltd., Beijing (CN); Lenovo (Beijing) Co., Ltd., Beijing (CN)

( * ) Notice: Subject to any disclaimer, the term of this patent is extended or adjusted under 35 U.S.C. 154(b) by 122 days.

(21) Appl. No.: 14/229,898

(22) Filed: Mar. 29, 2014

(65) Prior Publication Data

US 2015/0230717 A1 Aug. 20, 2015

(30) Foreign Application Priority Data

Feb. 19, 2014 (CN) .......................... 2014 1 0056880

(51) Int. Cl.
*G08B 1/08* (2006.01)
*G06F 19/00* (2011.01)
*A61B 5/145* (2006.01)
*A61B 5/021* (2006.01)
*A61B 5/024* (2006.01)

(52) U.S. Cl.
CPC ........ *G06F 19/3481* (2013.01); *G06F 19/3412* (2013.01); *A61B 5/021* (2013.01); *A61B 5/024* (2013.01); *A61B 5/14532* (2013.01)

(58) Field of Classification Search
CPC ........... A61B 5/02055; A61B 5/14532; A61B 5/742; A61B 5/021; A61B 5/024
USPC ........................................ 340/539.11–539.13
See application file for complete search history.

(56) References Cited

U.S. PATENT DOCUMENTS

| | | | | |
|---|---|---|---|---|
| 8,212,650 B2* | 7/2012 | Tsern | .................... | G06F 1/1626 340/3.1 |
| 8,517,896 B2* | 8/2013 | Robinette | .............. | A63B 24/00 702/160 |
| 8,784,115 B1* | 7/2014 | Chuang | .................. | A61B 5/486 600/300 |
| 2010/0016745 A1* | 1/2010 | Crump | ............... | A61B 5/02055 340/539.12 |
| 2010/0259407 A1* | 10/2010 | Tilvis | ................. | A63B 24/0062 340/686.6 |
| 2011/0169603 A1* | 7/2011 | Fithian | ................... | G06Q 10/00 340/5.52 |
| 2013/0041590 A1* | 2/2013 | Burich | ............... | G06F 19/3418 702/19 |
| 2013/0106684 A1* | 5/2013 | Weast | ................. | G06F 19/3481 345/156 |
| 2014/0087685 A1* | 3/2014 | Kellond | .................. | G06F 3/041 340/573.1 |
| 2014/0107493 A1* | 4/2014 | Yuen | ..................... | H04W 4/027 600/473 |
| 2015/0173674 A1* | 6/2015 | Hayes | .................... | A61B 5/681 600/301 |
| 2015/0182130 A1* | 7/2015 | Utter, II | ............... | A61B 5/0205 600/483 |

* cited by examiner

*Primary Examiner* — Eric Blount
(74) *Attorney, Agent, or Firm* — Harness, Dickey & Pierce, P.L.C.

(57) ABSTRACT

An information processing method and an electronic device are provided. The method is applied to the electronic device. The electronic device includes a frame structure, a display module, a processor and a first type of sensor. The method includes: obtaining a first type of data which reflects a physical performance of the first user and is captured by the first type of sensor, in the case that the electronic device is fixed on an operation portion of the first user through the frame structure and the electronic device is functioning; obtaining configuration information at least based on the first type of data; and automatically setting a second type of sensor different from the first type of sensor, and/or a display screen, and/or at least one piece of application data which may be fed back by the electronic device, to suit the physical performance of the first user.

6 Claims, 1 Drawing Sheet

INFORMATION PROCESSING METHOD AND ELECTRONIC DEVICE

CROSS REFERENCES OF RELATED APPLICATION

The present application claims the priority to Chinese Patent Application No. 201410056880.4, entitled "INFORMATION PROCESSING METHOD AND ELECTRONIC DEVICE", filed on Feb. 19, 2014 with the State Intellectual Property Office of People's Republic of China, which is incorporated herein by reference in its entirety.

FIELD

The disclosure relates to electronic technologies, and in particular, to an information processing method and an electronic device.

BACKGROUND

Thanks to the progresses in science and technologies, rapid developments take place in electronic devices. There exists a great variety of electronic products, and accordingly, people benefit from the convenience due to the progresses in science and technologies. Nowadays, with various electronic devices, people may enjoy a comfortable life brought by the progresses in science and technologies.

Conventionally, various sensors are arranged on smart phones, tablet computers and wearable devices. These sensors are all for detecting an environment in which an electronic device is located, so that the electronic device may be set and adjusted based on captured information to improve the intelligence of the electronic device.

Before the implementation of a technical solution of the disclosure, the inventor of the disclosure finds that the prior art has at least the following disadvantages.

No sensor for capturing the physical performance of a first user is provided in an existing electronic device. Hence, the physical performance of the first user may not be obtained, the electronic device may not be set based on the physical performance of the first user, and the experience of the first user is poor accordingly.

SUMMARY

An embodiment of the present disclosure provides an information processing method and an electronic device thereof, to address a disadvantage of existing technologies that an electronic device can not be set based on the physical performance of a first user, and the experience of the first user is improved accordingly.

An embodiment of the present disclosure provides an information processing method applied to an electronic device, where the electronic device includes: a frame structure, a display module, a processor and a first type of sensor, the frame structure includes a fixing structure, with which the electronic device is fixed on an operation portion of a first user, the display module including a display screen is fixed on the frame structure, the first type of sensor is fixed through the frame structure, and the processor is connected with the first type of sensor and is fixed through the frame structure;

where the method includes:
  obtaining a first type of data which reflects a physical performance of the first user and is captured by the first type of sensor, in the case that the electronic device is fixed on the operation portion of the first user through the frame structure and the electronic device is functioning;
  obtaining configuration information at least based on the first type of data; and
  automatically setting, based on the configuration information, a second type of sensor different from the first type of sensor, and/or the display screen, and/or at least one piece of application data which can be fed back by the electronic device, to suit the physical performance of the first user.

The electronic device further includes a third type of sensor different from the first type of sensor. Before the process of obtaining the configuration information at least based on the first type of data, the method further includes: obtaining a second type of data reflecting a location of the electronic device through the third type of sensor; where the process of obtaining the configuration information at least based on the first type of data includes: obtaining the configuration information based on the first type of data and the second type of data.

The process of obtaining the configuration information based on the first type of data and the second type of data includes:
  searching for first configuration information in a preset area around the location of the electronic device based on the second type of data; and selecting, from the first configuration information, the configuration information corresponding to the first type of data.

The process of obtaining the configuration information at least based on the first type of data includes: obtaining, at least based on the first type of data, the configuration information through cloud matching; or obtaining, at least based on the first type of data, the configuration information through another electronic device bound to the electronic device.

The first type of data is a heart rate and/or a temperature of the first user.

Another embodiment of the present disclosure provides an electronic device including:
  a frame structure, where the frame structure includes a fixing structure with which the electronic device is fixed on an operation portion of the first user;
  a display module fixed on the frame structure, where the display module includes a display screen;
  a first type of sensor fixed through the frame structure; and
  a processor connected with the first type of sensor and fixed through the frame structure; where the processor is configured to obtain a first type of data which reflects the physical performance of the first user and is captured by the first type of sensor, in the case that the electronic device is fixed on the operation portion of the first user through the frame structure and the electronic device is functioning; obtain configuration information at least based on the first type of data; and automatically set a second type of sensor different from the first type of sensor, and/or the display screen, and/or at least one piece of application data which may be fed back by the electronic device, to suit the physical performance of the first user.

The processor includes:
  a data obtaining unit, configured to obtain the first type of data which reflects the physical performance of the first user and is captured by the first type of sensor, in the case that the electronic device is fixed on the operation portion of the first user through the frame structure and the electronic device is functioning;

a configuration information obtaining unit, configured to obtain the configuration information at least based on the first type of data; and a setting unit, configured to automatically set, based on the configuration information, the second type of sensor different from the first type of sensor, and/or the display screen, and/or at least one piece of application data which may be fed back by the electronic device, to suit the physical performance of the first user reflected by the first type of data captured by the first type of sensor.

the electronic device further includes a third type of sensor different from the first type of sensor;

the data obtaining unit is further configured to obtain, through the third type of sensor, a second type of data reflecting a location of the electronic device, before obtaining the configuration information at least based on the first type of data; and the configuration information obtaining unit is further configured to obtain the configuration information based on the first type of data and the second type of data.

The configuration information obtaining unit is configured to, search for first configuration information in a preset area around the location of the electronic device based on the second type of data, and select, from the first configuration information, the configuration information corresponding to the first type of data.

The configuration information obtaining unit is configured to, obtain, at least based on the first type of data, the configuration information through cloud matching; or obtain, at least based on the first type of data, the configuration information through another electronic device bound to the electronic device.

The first type of data is a heart rate and/or a temperature of the first user.

The technical solutions according to the embodiments of the disclosure have at least the following technical effects or advantages.

The first type of sensor in the electronic device captures the first type of data, and the electronic device obtains the configuration information based on the first type of data. Then, the electronic device sets, based on the configuration information, the second type of sensor different from the first type of sensor, and/or the display screen, and/or at least one piece of application data which may be fed back by the electronic device, to suit the physical performance of the first user. That is, the electronic device captures the first type of data related to the body of the first user through the first type of sensor, and obtains corresponding configuration information based on the first type of data; then the electronic device may set, based on the configuration information, the second type of sensor, the display or one or more pieces of application data, to suit the physical performance of the first user. Hence, the disadvantage of existing technologies that the electronic device can not be set based on the physical performance of the first user is addressed, and the experience of the first user is improved accordingly.

DETAILED DESCRIPTION OF EMBODIMENTS

With an information processing method and an electronic device according to embodiments of the disclosure, a disadvantage of existing technologies that an electronic device can not be set based on the physical performance of a first user is addressed, and the experience of the first user is improved accordingly.

For addressing the above disadvantage, a technical solution according to the embodiments of the disclosure is as follows.

An electronic device captures a first type of data through a first type of sensor provided on the electronic device, and obtains configuration information based on the first type of data; then the electronic device sets, based on the configuration information, a second type of sensor different form the first type of sensor, and/or a display screen, and/or at least one piece of application data which may be fed back via the electronic device, to suit a physical performance of a first user. That is, the electronic device captures the first type of data related to the body of the first user through the first type of sensor, and obtains corresponding configuration information based on the first type of data; then the electronic device may set, based on the configuration information, one or more of the second type of sensor, the display screen and application data, to suit the physical performance of the first user. The disadvantage of existing technologies that the electronic device can not be set based on the physical performance of the first user is addressed, and the experience of the first user is improved accordingly.

For better understanding, the above technical solution is described in detail hereinafter in conjunction with drawings and the embodiments of the disclosure.

An information processing method is provided according to an embodiment of the disclosure. The method is applied to an electronic device. The electronic device may be a wearable device mounted on the body of a first user, for example, wrist watch, pocket watch, glasses, etc. The electronic device includes: a frame structure, a display module, a processor and a first type of sensor. The first type of sensor may be one or more sensors capable of detecting the physical performance of the first user, for example, heart rate sensor, temperature sensor, blood glucose sensor, blood pressure sensor, or any combination of these different types of sensors, which is not limited in the disclosure. The frame structure includes a fixing structure, with which the electronic device may be fixed on an operation portion of the first user. The display module is fixed on the frame structure. The display module includes a display screen. The first type of sensor is fixed through the frame structure. The processor is connected with the first type of sensor and fixed through the frame structure.

Figure 1:
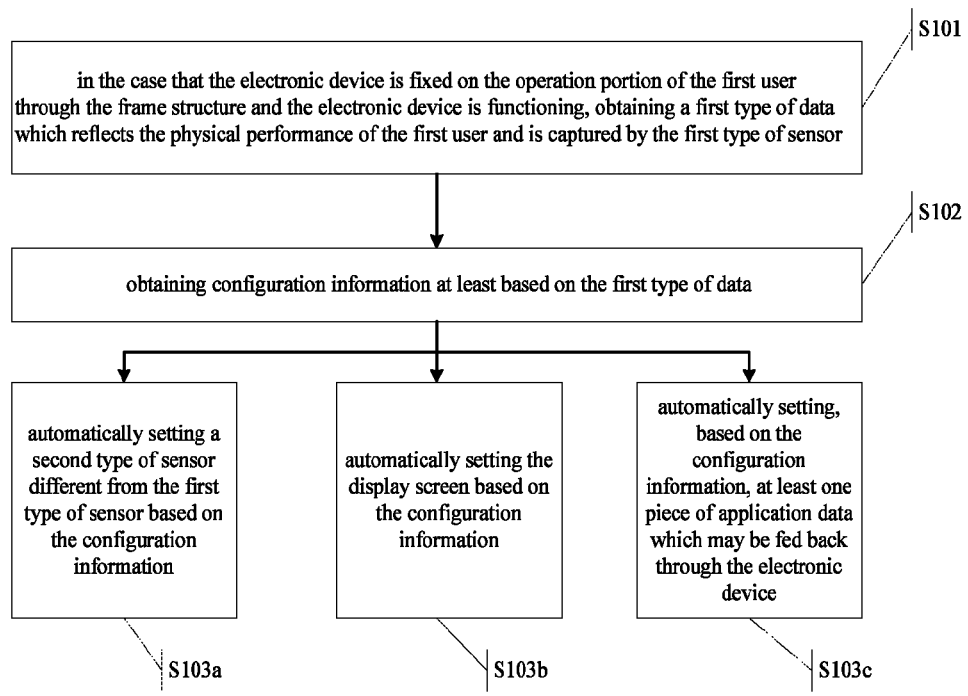
FIG. 1 is a flowchart of an information processing method according to an embodiment of the disclosure.

As shown in FIG. 1, the method includes the following steps.

In a step S101, in the case that the electronic device is fixed on the operation portion of the first user through the frame structure and the electronic device is operating, a first type of data, which reflects the physical performance of the first user and is captured by the first type of sensor, is obtained.

In a step S102, configuration information is obtained at least based on the first type of data.

In practice, the step after the step S102 may have the following implementations, while it is not limited to these implementations.

In a first implementation, the method after the step S102 includes a step S103a: automatically setting a second type of sensor different from the first type of sensor based on the configuration information, to suit the physical performance of the first user.

In a second implementation, the method after the step S102 includes a step S103b: automatically setting the display screen based on the configuration information, to suit the physical performance of the first user.

In a third implementation, the method after the step S102 includes a step S103c: automatically setting, based on the configuration information, at least one piece of application data which may be fed back through the electronic device, to suit the physical performance of the first user.

The steps S103a to S103c may be combined, which are not limited in the disclosure, The above solution is explained with an example that the electronic device is an intelligent watch.

Firstly, in the case that the electronic device is fixed on the operation portion of the first user through the frame structure and the electronic device is functioning, that is, in the case that the intelligent watch is fixed around a wrist of the first user through a strap and the intelligent is functioning, the step S101 is performed. That is, the first type of data, which reflects the physical performance of the first user and is captured by the first type of sensor, is obtained. For example, in the case that the first type of sensor is a heart rate sensor, the step 101 is to obtain the first type of data captured by the heart rate sensor, i.e., a heart rate of the first user. Alternatively, in the case that the first type of sensor is a temperature sensor, the step 101 is to obtain the first type of data captured by the temperature sensor, i.e., a temperature of the first user. Obviously, in the case that the first type of sensor is a blood glucose sensor or a blood pressure sensor, the first type of data is respectively a blood glucose level or a blood pressure of the first user, which is not limited in the disclosure.

Then, the step S102 is performed. That is, the configuration information is obtained at least based on the first type of data.

In practice, since only the first type of data is obtained by the electronic device, the electronic device may obtain, based on the first type of data, the configuration information through cloud matching. For example, in the case that the first type of data obtained in the step S101 is the heart rate of the first user, the electronic device may send the heart rate to a cloud. The cloud may perform matching for the heart rate in a data base of the cloud, and find that the first user may suffer the coronary heart disease and should exercise. Here, a necessary exercise intensity for the first user, such as the configuration information of a distance for brisk walking, steps for jogging, or the like, is determined, and then sent to the electronic device. The electronic device receives the configuration information.

According to another embodiment of the disclosure, the configuration information is obtained through another electronic device bound to the electronic device based on the first type of data. For example, if the electronic device is bound to a smart phone of the first user, the electronic device sends the first type of data to the smart phone after obtaining the first type of data. The smart phone sends the first type of data to the cloud to perform matching, or the configuration information corresponding to the first type of data is found by searching the internet with the smart phone.

In the end, the step S103a is performed. The second type of sensor such as a pedometer, an acceleration sensor, etc., which is different from the first type of sensor, is automatically set based on the configuration information to suit the physical performance of the first user. That is, the electronic device sets the second type of sensor based on the configuration information. For example, if the configuration information indicates 100 steps of brisk walking, the electronic device sets a count of 100 for the pedometer.

According to another embodiment, the step S103b is performed after the step S102. That is, the display screen is automatically set based on the configuration information to suit the physical performance of the first user.

The electronic device sets the display screen based on the configuration information obtained in the step S102, such as, contents displayed on the display screen are adjusted or a brightness of the display screen is changed. For example, if the configuration information obtained in the step S102 is prompt information indicating "100 steps of brisk walking", here the prompt information is displayed on the display screen to prompt the first user to walk 100 steps. Precautions for the coronary heart disease may further be displayed on the display screen.

Obviously, the step S103b may be combined with the step S103a, therefore, the second type of sensor is set while setting the display screen. The count for the pedometer is set as 100 and a value of remaining steps is displayed in a realtime manner. When the first user finishes 100 steps, notification information is displayed on the display screen to inform that the brisk walking is already finished. Alternatively, the first user may be informed, through voice information, of the accomplishment of the brisk walking. Furthermore, when the first user finishes 100 steps, the electronic device may vibrate to prompt the first user.

According to another embodiment of the disclosure, the step S103c is performed after the step S102. That is, at least one piece of application data which may be fed back through the electronic device is automatically set based on the configuration information to suit the physical performance of the first user.

In practice, many applications may be installed in the electronic device, such as, applications related to recipes, maps, medicines, etc. The electronic device may set data of the applications based on the configuration information obtained in the step S102, and the data may be fed back to the first user through the electronic device. For example, the configuration information obtained by the electronic device in step S102 indicates setting a recipe type in an application related to recipes as "recipes for the coronary heart disease sufferers", the electronic device changes the recipe type in the application related to recipes. When the first user uses the application to choose recipes, the application may preferentially feed back information of food with low contents of iron elements, salinity and fat to the first user with emails, messages or the like. Furthermore, in the case that the step S103c is combined with the step S103b, the information of the eligible food is displayed on the display screen.

Furthermore, the electronic device may include one or more third type of sensors such as Global Position System (GPS) modules, gravitational acceleration sensors, gyroscopes, altitude sensors, etc. The third type of sensor(s) is adapted to detect information of a location of the electronic device, for example, the longitude and latitude of the electronic device, an altitude of the electronic device, and a location of the electronic device on a map.

Accordingly, the method according to the foregoing one or more embodiments further includes: obtaining a second type of data reflecting the location of the electronic device, through the third type of sensor(s).

Here, the step S102 may include: obtaining the configuration information based on the first type of data and the second type of data. That is, the electronic device, on receiving the first type of data in the step S101, may further receive the second type of data through the third type of sensor(s). The electronic device sends the two types of data to the cloud or to another electronic device bound to the electronic device, to obtain the configuration information corresponding to the two types of data.

For example, the first type of data obtained by the electronic device indicates that the temperature or heart rate of the first user is too high, and the second type of data indicates that the first user is currently at an altitude of 3500 meters, the cloud or the another electronic device may send the configuration information of "The first user suffers the altitude sickness" to the electronic device.

In this situation, the electronic device may display the notification information of "Take in oxygen please" on the display screen by performing the step S103b. Further, the electronic device may set a medicine type in an application related to medicines as anti-altitude sickness medicines. When the first user runs the application, the application preferentially feeds back information of the anti-altitude sickness medicines to the first user, or the application pushes the information of the anti-altitude sickness medicines to the first user. Preferably, the step S103b and the step S103c are combined, and the information of the anti-altitude sickness medicines is displayed on the display screen.

In practice, alternatively, the process of obtaining the configuration information based on the first type of data and the second type of data may include: searching for first configuration information in a preset area around the location of the electronic device; and selecting the configuration information corresponding to the first type of data, from the first configuration information.

For example, the electronic device obtains, based on the second type of data, i.e., the location of the electronic device, information of all shops in the preset area around the location, e.g., in a 500-meter radius of the location. The information of all the shops is the first configuration information. The electronic device determines, based on the first type of data, i.e., the heart rate of the first user, that the first user has a high blood pressure and would better eat vegetables, and accordingly, the electronic device determines, form the first configuration information, the configuration information corresponding to the first type of data, i.e., the information of all vegetarian restaurants. Then the step S103b may be performed, that is, the information of the vegetarian restaurants is displayed on the display screen.

With the above description, the first type of sensor in the electronic device captures the first type of data, and the electronic device obtains the configuration information based on the first type of data; then, the electronic device sets, based on the configuration information, the second type of sensor different from the first type of sensor, and/or the display screen, and/or at least one piece of application data which may be fed back by the electronic device, to suit the physical performance of the first user. That is, the electronic device captures the first type of data related to the body of the first user through the first type of sensor, and obtains corresponding configuration information based on the first type of data; then the electronic device may set, based on the configuration information, the second type of sensor, the display screen or one or more pieces of application data, to suit the physical performance of the first user, and accordingly, the experience of the first user is improved.

Figure 2:
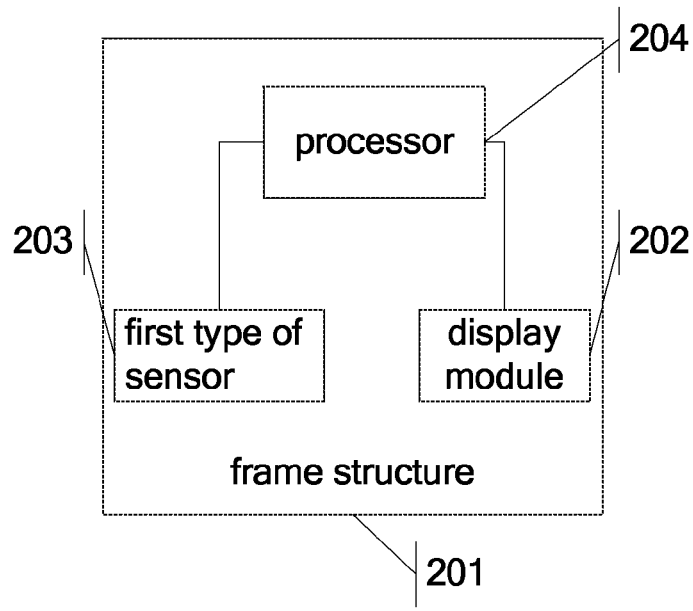
FIG. 2 is a functional structure diagram of an electronic device according to an embodiment of the disclosure.

An electronic device is further provided according to an embodiment of the disclosure. The electronic device may be a wearable device mounted on the body of a first user, for example, wrist watch, pocket watch, glasses, etc. As shown in FIG. 2, the electronic device includes: a frame structure 201, a display module 202, a first type of sensor 203 and a processor 204. The frame structure 201 includes a fixing structure, with which the electronic device may be fixed on an operation portion of the first user. The display module 202, including a display screen, is fixed on the frame structure 201. The first type of sensor 203 is fixed through the frame structure 201. The processor 204 is connected with the first type of sensor 203 and fixed through the frame structure 201. The processor 204 is configured to obtain a first type of data, which reflects the physical performance of the first user and is captured by the first type of sensor 203, in the case that the electronic device is fixed on the operation portion of the first user through the frame structure 201 and the electronic device is functioning; obtain configuration information at least based on the first type of data; and automatically set a second type of sensor different from the first type of sensor 203, and/or the display screen, and/or at least one piece of application data which may be fed back by the electronic device, to suit the physical performance of the first user.

Furthermore, the processor 204 includes a data obtaining unit, a configuration information obtaining unit and a setting unit. The data obtaining unit is configured to, in the case that the electronic device is fixed on the operation portion of the first user through the frame structure 201 and the electronic device is functioning, obtain the first type of data which reflects the physical performance of the first user and is captured by the first type of sensor 203. The configuration information obtaining unit is configured to obtain the configuration information at least based on the first type of data. The setting unit is configured to automatically set the second type of sensor different from the first type of sensor 203, and/or the display screen, and/or at least one piece of application data which may be fed back by the electronic device, to suit the physical performance of the first user reflected by the first type of data captured by the first type of sensor 203.

Furthermore, the electronic device further includes a third type of sensor different from the first type of sensor. The data obtaining unit is further configured to obtain, through the third type of sensor, a second type of data reflecting a location of the electronic device. The configuration information obtaining unit is further configured to obtain the configuration information based on the first type of data and the second type of data.

Furthermore, the configuration information obtaining unit is configured to, search for first configuration information in a preset area around the location of the electronic device based on the second type of data, and select the configuration information corresponding to the first type of data from the first configuration information.

Furthermore, the configuration information obtaining unit is configured to, obtain, at least based on the first type of data, the configuration information through cloud matching; or obtain, at least based on the first type of data, the configuration information through another electronic device bound to the electronic device.

Furthermore, the first type of data is a heart rate and/or a temperature of the first user.

Since the electronic device provided in the disclosure is used in the information processing method provided in the disclosure, implementations and variations of the electronic device according to the embodiment of the disclosure may be known by those skilled in the art based on the information processing method provided in the disclosure. Therefore, the electronic device is not described in detail. Any implementation of the electronic device used in the information processing method provided in the disclosure should fall in the scope of protection of the disclosure.

The technical solution according to the embodiments of the disclosure has at least the following technical effect or advantage.

The first type of sensor in the electronic device captures the first type of data, and the electronic device obtains the configuration information based on the first type of data. Then, the electronic device sets, based on the configuration information, the second type of sensor different from the first type of sensor, and/or the display screen, and/or at least one piece of application data which may be fed back by the electronic device, to suit the physical performance of the first user. That is, the electronic device captures the first type of data related to the body of the first user through the first type of sensor, and obtains corresponding configuration information based on the first type of data; then the electronic device may set, based on the configuration information, the second type of sensor, the display or one or more pieces of application data, to suit the physical performance of the first user. Hence, the disadvantage of existing technologies that the electronic device can not be set based on the physical performance of the first user is addressed, and the experience of the first user is improved accordingly.

It should be understood by those skilled in the art that, the embodiments according to the present disclosure may be implemented as a method, system or computer program product. Hence, the embodiments of the invention may be implemented with hardware only, with software only, or with a combination of hardware and software. Furthermore, the embodiments of the present disclosure may be embodied as computer program products implemented on one or more computer readable media (including but not limited to magnetic disk storage, CD-ROM, optical storage, etc.) including computer executable codes.

The description in this disclosure is made in conjunction with flowchart(s) and/or block diagram(s) of the method, device (system) or computer program product according to the embodiments of the disclosure. It should be understood that each process in the flowchart and/or each block in the block diagram and any combination of processes and/or blocks in the flowchart and/or the block diagram may be implemented through computer program instructions. The computer instructions may be provided to a processor of a general-purpose computer, dedicated computer, embedded processing machine or any other programmable data processing device to generate a machine, in which device(s) to implement functions specified in one or more processes of the flowchart and/or one or more blocks of the block diagram are implemented through executing the instructions by the computer or any other programmable data processing device.

The computer program instructions may further be stored in a computer readable storage which may lead the computer or any other programmable data processing device to operation in particular manner in order that a product including an instruction device is generated according to the instructions stored in the computer readable storage, where the instruction device is configured to implement the functions specified in one or more processes of the flowchart and/or one or more blocks of the block diagram.

The computer program instructions may further be loaded to the computer or any other programmable data processing device in order that a series of steps are executed on the computer or any other programmable data processing device to generate processes implemented by the computer, and the steps to implement the functions specified in one or more processes of the flowchart and/or one or more blocks of the block diagram are provided by the instructions executed on the computer or any other programmable data processing device.

The computer program instructions corresponding to the information processing method according to the embodiments of the disclosure may be stored in storage media such as optical storage, hard disk, USB flash disk, etc. In the case that the computer program instructions corresponding to the information processing method are read or executed by an electronic device, the following processes are performed: in the case that the electronic device is fixed on an operation portion of a first user through a frame structure and the electronic device is functioning, obtaining a first type of data which reflects the physical performance of the first user and is captured by a first type of sensor; obtaining configuration information at least based on the first type of data; and automatically setting a second type of sensor different from the first type of sensor, and/or a display screen, and/or at least one piece of application data which may be fed back by the electronic device, to suit the physical performance of the first user.

Optionally, some other computer instructions are stored in the storage media. These computer instructions are executed before the step of obtaining the configuration information at least based on the first type of data. When executing these computer instructions, the following process is performed: obtaining, through a third type of sensor, a second type of data reflecting a location of the electronic device. The process of obtaining the configuration information at least based on the first type of data may include: obtaining the configuration information based on the first type of data and the second type of data.

Optionally, the process of obtaining the configuration information based on the first type of data and the second type of data includes: searching for first configuration information in a preset area around the location of the electronic device based on the second type of data; and selecting the configuration information corresponding to the first type of data from the first configuration information.

Optionally, the process of obtaining the configuration information at least based on the first type of data includes: obtaining, at least based on the first type of data, the configuration information through cloud matching; or obtaining, at least based on the first type of data, the configuration information through another electronic device bound to the electronic device.

Although preferred embodiments of the disclosure are described, alterations and variations may be made to those embodiments by those skilled in the art once the basic conception of the disclosure is acquired. Therefore, claims of the disclosure are intended to protect the preferred embodiments and all the alterations and variations falling in the scope of the disclosure.

Obviously, various alterations and variations may be made by those skilled in the art without departing form the spirit and scope of the disclosure. Hence, the disclosure is intended to include all the alterations and variations falling in the scope of the disclosure or equivalent technologies.

The invention claimed is:

1. An information processing method applied to an electronic device, wherein:
   the electronic device includes a frame structure, a display module, a processor, and a first type of sensor;
   the frame structure includes a fixing structure that fixes the electronic device on an operation portion of a first user;
   the display module includes a display screen and is fixed on the frame structure
   the first type of sensor is fixed through the frame structure;
   the processor is connected with the first type of sensor and is fixed through the frame structure;
   the method comprises:
      obtaining a first type of data that reflects a physical performance of the first user and is captured by the first type of sensor, in a case that (i) the electronic device is fixed on the operation portion of the first user through the frame structure and (ii) the electronic device is functioning;

obtaining configuration information at least based on the first type of data; and automatically setting, based on the configuration information, a second type of sensor different from the first type of sensor, and/or the display screen, and/or at least one piece of application data that can be fed back by the electronic device, to suit the physical performance of the first user;

the electronic device further includes a third type of sensor different from the first type of sensor;

the method further includes, before obtaining the configuration information, obtaining a second type of data reflecting a location of the electronic device through the third type of sensor, and obtaining the configuration information includes:
   searching for first configuration information in a preset area around the location of the electronic device based on the second type of data; and
   selecting, from the first configuration information, the configuration information corresponding to the first type of data.

2. The method according to claim 1, wherein obtaining the configuration information comprises at least one of:
   obtaining, at least based on the first type of data, the configuration information through cloud matching; and
   obtaining, at least based on the first type of data, the configuration information through another electronic device bound to the electronic device.

3. The method according to claim 1, wherein the first type of data is a heart rate and/or a temperature of the first user.

4. An electronic device comprising:
   a frame structure, wherein the frame structure comprises a fixing structure that fixes the electronic device on an operation portion of a first user;
   a display module fixed on the frame structure, wherein the display module comprises a display screen;
   a first type of sensor fixed through the frame structure;
   a processor connected with the first type of sensor and fixed through the frame structure, wherein the processor comprises:
      a data obtaining unit configured to obtain a first type of data that reflects a physical performance of the first user and is captured by the first type of sensor, in a case that the electronic device is fixed on the operation portion of the first user through the frame structure and the electronic device is functioning;
      a configuration information obtaining unit configured to obtain configuration information at least based on the first type of data; and
      a setting united configured to automatically set a second type of sensor different from the first type of sensor, and/or the display screen, and/or at least one piece of application data that may be fed back by the electronic device, to suit the physical performance of the first user; and
   a third type of sensor different from the first type of sensor,
   wherein the data obtaining unit is further configured to, before obtaining the configuration information, obtain, through the third type of sensor, a second type of data reflecting a location of the electronic device; and
   wherein the configuration information obtaining unit is further configured to search for the first configuration information in a preset area around the location of the electronic device based on the second type of data, and select, from the first configuration information, the configuration information corresponding to the first type of data.

5. The electronic device according to claim 4, wherein the configuration information obtaining unit is configured to at least one of:
   obtain, at least based on the first type of data, the configuration information through cloud matching; and
   obtain, at least based on the first type of data, the configuration information through another electronic device bound to the electronic device.

6. The electronic device according to claim 4, wherein the first type of data is a heart rate and/or a temperature of the first user.

* * * * *